United States Patent [19]

Soike

[11] Patent Number: 5,059,418
[45] Date of Patent: Oct. 22, 1991

[54] SYNERGISTIC EFFECT OF HUMAN RECOMBINANT INTERFERON-BETA ON HALOGENATED PYRIMIDINES

[75] Inventor: Kenneth F. Soike, Covington, La.

[73] Assignee: The Administrators of the Tulane Educational Fund, New Orleans, La.

[21] Appl. No.: 410,164

[22] Filed: Sep. 20, 1989

[51] Int. Cl.$^5$ ...................... C07H 19/06; A61K 37/66
[52] U.S. Cl. .................................... 424/85.6; 514/49; 424/85.4; 424/85.5; 424/85.7
[58] Field of Search ..................... 424/85.4, 85.5, 85.6, 424/85.7; 514/49

[56] References Cited

U.S. PATENT DOCUMENTS

| | | | |
|---|---|---|---|
| 4,289,689 | 9/1981 | Friesen et al. | 424/85 |
| 4,588,585 | 5/1986 | Mark et al. | 424/85 |
| 4,666,892 | 5/1987 | Fox et al. | 514/49 |

OTHER PUBLICATIONS

Hu et al., *J. Biol. Resp. Mod.* 6:121–129 (1987).
Melvin D. Trousdale et al., "Activity of 1-(2'-Fluoro-2'-Deoxy-$\beta$-D-Arabinofuranosyl) Thymine Against Herpes Simplex Virus in Cell Cultures and Rabbit Eyes", Antimicrobial Agents and Chemotherapy 23(6): 808–813 (Jun. 1983).
Raymond F. Schinazi et al., "Therapeutic Activities of 1-(2-Fluoro-2-Deoxy-$\beta$-D-Arabinofuranosyl)-5-Iodocytosine and -Thymine Alone and in Combination with Acyclovir and Vidarabine in Mice Infected Intracerebrally with Herpes Simplex Virus", Antimicrobial Agents and Chemotherapy 24(1): 95–103 (Jul. 1983).
Deborah A. Eppstein et al., "Patent Synergistic Inhibition of Herpes Simplex Virus-2 by 9-[(1,3-Dihydroxy-2-propoxy)methyl] quanine in Combination with Recombinant Interferons", Biochemical and Biophysical Research Communications 120 (1): 66–73 (Apr. 16, 1984).
Ting-Chao Chou et al., "Quantitative Analysis of Dose-Effect Relationshps: The Combined Effects of Multiple Drugs or Enzyme Inhibitors", Advances in Enzyme Regulation, George Weber editor, 22: 27–55 (1983).
Michael P. Fanucchi et al., "Phase I Trial of 1-(2'-Deoxy-2'-Fluoro-1-$\beta$-D-Arabinofuranosyl)-5-Methyluracil (FMAU)", Cancer Treatment Reports 69(1): 55–59 (Jan., 1985).
J. J. Fox et al., "Antiviral Activities of Some Newer 2-'Fluoro-5-Substituted Arabinosylpyrimidine Nucleosides", Herpes Viruses and Virus Chemotherpay, R. Kono and A. Nakajima editors, pp. 53–56 (1985).
Donald R. Mayo et al., "Treatment of Primary Acute Genital Herpes in Guinea Pigs by Intraperitoneal Administration of Fluoroyrimidines", Antimicrobial Agents and Chemotherapy 26(3): 354–357 (1984).
Kenneth F. Soike et al., "Activity of 1-(2'-Deoxy-2'--Fluoro-$\beta$-D-Arabinofuranosyl)-5-Iodouracil Against Simian Varicella Virus Infections in African Green Monkeys, Antimicrobial Agents and Chemotherapy" 29(1): 20–25 (Jan. 1986).
Ting-Chao et al., "Synthesis and Biological Effects of 2'-Fluoro-5-Ethyl-1-$\beta$-D-Arabinofuranosyluracil", Antimicrobial Agents and Chemotherapy 31(9): 1355–1358 (Sep. 1987).
Kenneth F. Soike et al., "Effect of 9-(1,3-Dihydroxy-2-Propoxymethyl) Guanine and Recombinant Human $\beta$ Interferon Alone and in Combination on Simian Varicella Virus Infection in Monkeys", The Journal of Infectious Diseases 156(4): 607–614 (Oct. 1987).

*Primary Examiner*—Margaret Moskowitz
*Assistant Examiner*—Shelly J. Guest
*Attorney, Agent, or Firm*—Shelley G. Precivale; Al A. Jecminek; Karen Babyak Dow

[57] ABSTRACT

A method of treating patients having viral infections exhibiting a synergistic antiviral effect in combination therapy of viral infections is comprised of combining synergistically effective amounts of a halogenated pyrimidine and human recombinant interferon-beta, said agents to be delivered separately or as a single combined composition of matter.

31 Claims, No Drawings

SYNERGISTIC EFFECT OF HUMAN RECOMBINANT INTERFERON-BETA ON HALOGENATED PYRIMIDINES

FIELD OF THE INVENTION

This invention relates to combination therapy exhibiting a synergistic antiviral effect on human viral infections comprising administering a halogenated pyrimidine and human recombinant interferon-beta. More particularly, this invention relates to combination therapy which exhibits a synergistic biological effect combining administering 1-(2'-deoxy-2'-fluoro-1-β-D-arabinofuranosyl)-5-ethyl uracil and human recombinant interferon-beta.

BACKGROUND OF THE INVENTION

Prior studies with halogenated pyrimidines such as the fluorinated pyrimidines 1-(2'-deoxy-2'-fluoro-1-β-D-arabinofuranosyl)-5-iodouracil (FIAU) and 1-(2'-deoxy-2'-fluoro-1-β-D-arabinofuranosyl)-5-methyl uracil (FMAU) have indicated that these compounds are highly effective inhibitors of simian varicella virus both in vitro and in vivo in African green monkeys. Soike et al., Antimicrob. Agents Chemother. 29: 20–25 (1986). FIAU at oral doses of 3 mg/kg/day prevented development of simian varicella rash in monkeys and appreciably reduced viremia while FMAU was highly effective in preventing rash and viremia in monkeys at doses as low as 0.2 mg/kg/day. Unfortunately central nervous system toxicity observed in patients with advanced cancer treated with FMAU restricted its further consideration for antiviral applications.

Synthesis of analogs of FMAU resulted in the selection of the ethyl analog 1-(2'-deoxy-2'-fluoro-1-β-D-arabinofuranosyl)-5-ethyl uracil (FEAU) as a potential antiviral agent with a more favorable therapeutic index. Chou et al., Antimicrob. Agents Chemother. 31:1355–1358 (1987). Although FEAU was slightly less active than FMAU in inhibiting herpes simplex virus infection in Vero cells and in mice, FEAU was also much less toxic. Fox et al., in *Herpes Viruses and Virus Chemotherapy*, pp. 53–56 (Elsevier Science Publishing, Inc., New York, 1985).

It has been shown that FEAU, as with FIAU and FMAU, is a highly effective inhibitor of simian varicella virus in the African green monkey. Activity of FEAU against simian varicella virus was comparable to that reported for FIAU but less than FMAU.

Similar levels of activity have been reported for the fluorinated pyrimidines in the treatment of herpes simplex virus infection in other animal models, U.S. Pat. No. 4,666,892. Trousdale et al., Antimicrob. Agents Chemother. 23:808–813 (1983) showed topical treatment of rabbit eyes infected with the McKrae strain of HSV-1 with solutions of FMAU reduced corneal infection. Mice infected by intracerebral inoculation of HSV-1 (KOS strain) were protected from death by both 1-(2'-deoxy-2'-fluoro-1-β-D-arabinofuranosyl)-5-iodocytosine (FIAC) and FMAU. Schinazi et al., Antimicrob. Agents Chemother. 24:95-103 (1983). FIAC and FMAU were also successful in treating HSV-2 infection in guinea pigs, although higher doses were required. Mayo et al., Antimicrob. Agents Chemother. 26:354–357 (1984). Evaluation of FEAU in these animal models has not been reported.

Halogenated pyrimidines such as the fluorinated pyrimidines are highly effective antiviral and would be expected to have great potential for the treatment of human viral infections. FEAU was of particular interest because of its reported low toxicity. It was therefore attempted to determine whether the effective antiviral dose of FEAU might be further reduced by combination of FEAU with another antiviral active against simian varicella virus.

Interferons constitute a group of naturally occurring proteins which possess antiviral, antitumor and immunoregulatory properties. Two types of interferons have been identified based upon differences in their observed biological properties and molecular structures: Type I and Type II. Of particular interest was interferon-beta, a Type I interferon which could be induced in fibroblasts by viral challenge and contained 165 amino acids. Because human native interferon is expensive to extract, techniques have been developed for preparing recombinant forms of human interferon. Sugano et al., European Patent Publication No. 28,033 published June 6, 1981, have developed a technique for inserting a recombinant plasmid containing the human interferon-beta gene into a host microorganism, preferably *E. coli,* to obtain a transformant which expresses recombinant interferon-beta. However, the transformed *E. coli* contains multimers so purification and isolation of the interferon-beta is difficult. European Patent Publication No. 109,748 published May 30, 1984 describes a human interferon-beta mutein ($IFN\beta_{ser17}$) which has a cysteine residue at amino acid position 17 replaced by a serine residue to eliminate the problems of purification, along with improving the potency and stability of interferon-beta. Human $IFN\beta_{ser17}$ has been combined with 9-(1,3-dihydroxy-2-propoxy)methyl guanine (DHPG) to form a composition synergistically effective in inhibiting herpes simplex virus (HSV-2) as reported by Eppstein et al. in Biochemical and Biophysical Research Communications 120: 66–73 (1984). More recently it was shown by Soike et al. in Journal of Infectious Diseases 156: 607–614 (1987) that combining low doses of human recombinant interferon-beta (Hu rIFNβ) with DHPG reduced the effective dose of DHPG tenfold.

In view of FEAU's low toxicity and effectiveness in treating viral infections and the established antiviral properties of Hu rIFNβ, it would be useful to investigate whether their combination would provide a synergistic effect in treating human viral infections, using the African green monkey as an animal model.

SUMMARY OF INVENTION

Accordingly, the present invention is directed to combination therapy and method of treating patients having viral infections, having a synergistic antiviral effect on viral infections which comprises administering synergistically effective amounts of a halogenated pyrimidine such as 1-(2'-deoxy-2'-fluoro-1-β-D-arabinofuranosyl)-5-ethyl uracil (FEAU) and human recombinant interferon-beta (Hu rIFNβ).

This invention is also directed to a composition having a synergistic antiviral effect on human patients infected with viral infections such as herpes simplex virus, which comprises synergistically effective amounts of FEAU and Hu rIFNβ.

In another embodiment, the invention relates to an improved method for treating human viral infections with a halogenated pyrimidine such as FEAU wherein the improvement comprises treating human patients with FEAU having a synergistic antiviral effect in a treatment comprising synergistically effective amounts of a halogenated pyrimidine and pharmaceutically pure Hu rIFNβ. Treatment can be either as a combined therapeutic composition or as separate treatments.

A further aspect of this invention resides in the combined therapeutic composition which comprises said amounts of FEAU and Hu rIFNβ as well as an effective amount of a pharmaceutically acceptable diluent or carrier.

DESCRIPTION OF THE INVENTION

By the term "human recombinant interferon-beta" (Hu rIFNβ) is meant human interferon-beta produced by recombinant DNA techniques wherein generally the gene coding for human interferon-beta is cloned by known recombinant DNA technology such as by using human interferon-beta messenger RNA as a template, the gene showing complementarity to human interferon-beta messenger RNA is inserted in a suitable vector DNA such as an *E. coli* plasmid to obtain a recombinant plasmid, and the plasmid is used to transform a suitable host. The gene is expressed in the host to product the recombinant protein. Examples of suitable recombinant plasmids include pBR322, pCR1, pMB9 and pSC1. The transformed host can be either eucaryotic or procaryotic. The preferred host is *E. coli* or Chinese hamster ovary cells. Techniques for preparing human recombinant interferon-beta are described in EP 28,033 published June 6, 1981 to Sugano et al. and U.K. 2,063,882 published June 10, 1981 to Revel et al. The preferred Hu rIFNβ is a mutein of biologically active human interferon-beta in which the cysteine residue which is not essential to biological activity is deleted or replaced with other amino acids to eliminate sites for intermolecular crosslinking or incorrect intramolecular disulfide bond formation. More preferably, the mutein has the cysteine residue at position 17 or the native interferon-beta sequence, replaced by a serine residue (Hu rIFN-$\beta_{ser17}$). This mutein is described in U.S. Pat. No. 4,588,585, incorporated herein by reference.

The term "pharmaceutically pure" refers to Hu rIFNβ as defined above which is suitable for unequivocal biological testing as well as for appropriate administration to effect treatment of a human patient. Substantially pharmaceutically pure means at least about 90% pharmaceutically pure. One method by which Hu IFNβ may be purified from the transformed host which has been fermented in appropriate media is described as follows and enables yields of Hu IFNβ in greater than 90% purity: concentration of the harvest material, disruption of the cell suspension, extraction of the cells with 2-butanol, acid precipitation, chromatographic purification using S-200 pre-column, oxidation using iodosobenzoic acid, passage through S-200 main column, passage through G-75 column, desalting on G-25 column, formulation with normal serum albumin and dextrose, and lyophilization.

The term "synergistically effective amounts" of a halogenated pyrimidine and Hu rIFNβ refers to amounts of each component in the treatment which are effective in producing more than the additive effect of each component.

The difference between synergy and additivity can often be difficult to ascertain. One method of measuring synergy is to evaluate drug interactions using a combination index (CI), which is explained in detail in Soike et al., The Journal of Infectious Diseases 156(4):607-614 (1987) and in Chou et al., Advances in Enzyme Regulation, 22: 27-55 (1984), both of which are incorporated herein by reference. The combination index is calculated by the following equation:

$$CI = [(D)_1/(D_x)_1] + [(D)_2/(D_x)_2] + [\alpha(D)_1 \times (D)_2/(D_x)_1 \times (D_x)_2]$$

where:
$(D_x)_1$ = the dose of drug 1 required to produce X% effect alone
$(D)_1$ = the dose of drug 1 needed to produce the same X% effect in combination with $(D)_2$
$(D_x)_2$ = the dose of drug 2 needed to produce X% effect alone
$(D)_2$ = the dose of drug 2 required to produce the same X% effect in combination with $(D)_1$ CI values of 1 indicate additive effects, values of <1 indicate synergy and values of >1 reveal antagonism. When the effects of two drugs are mutually exclusive, for example, have the same mode of action, $\alpha = 0$ and the CI value is simply the sum of the first two terms. When the effects of two drugs are mutually non-exclusive and have different or independent modes of action, $\alpha = 1$ and the CI value is the sum of all three terms.

As used herein, "halogenated pyrimidine" is used to denote a 5-substituted-1-(2'-deoxy-2'-substituted-β-D-arabinofuranosyl) pyrimidine compound of the formula:

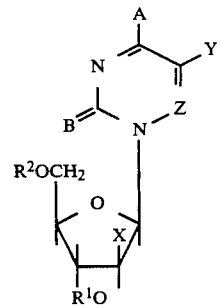

wherein
A is $OR^3$, $SR^3$, $NR^3R^4$ or NHacyl wherein $R^3$ and $R^4$ are the same or different and are hydrogen, lower alkyl of 1 to 7 carbon atoms, aralkyl, or aryl;
NHacyl is alkanoyl or aroyl amide:
B is oxygen or sulfur;
X is halogen;
Y is halogen, amino, monoalkyl- or monoaralkylamino, dialkylamino, aminomethyl, hydroxymethyl, lower alkyl, aryl, aralkyl, vinyl and substituted vinyl or ethynyl and substituted ethynyl,
Z is methyne or nitrogen; and
$R^1$ and $R^2$ are the same or different and are hydrogen, acyl or aroyl.

Particularly suitable for use is this invention are the fluorinated pyrimidines, FEAU, FIAU, FMAU and FIAC. The general chemical formula for these compounds as set forth above is described in detail in U.S. Pat. No. 4,666,892, incorporated herein by reference.

The halogenated pyrimidine and Hu rIFNβ may be combined using any suitable technique and may be used sequentially or simultaneously where the halogenated pyrimidine is orally administered and Hu rIFNβ is given parenterally such as subcutaneously, or intravenously or intramuscularly. However, this invention encompasses administering either agent via oral, parenteral or topical dosages.

Depending upon the desired route of administration, the halogenated pyrimidine and Hu rIFNβ compositions used may be in the form of solid, semi-solid or liquid such as tablets, pills, powders, capsules, gels, ointments, liquids, suspensions or the like. In the preferred embodiment, the agents are administered in unit dosage forms suitable for single administration of precise dosage amounts. The compositions may also include pharmaceutically acceptable carriers or diluents such as aqueous based vehicles commonly utilized in pharmaceutical formulations for treatment of animals and humans. The diluent is selected so as not to affect the biological activity of the agents, especially Hu rIFNβ. Suitable diluents include, without limitation, distilled water, physiological saline, Ringer's solution, dextrose solution and Hank's solution. Additionally, the pharmaceutical compositions may also include other pharmaceutical agents, carriers, adjuvants, and non-therapeutic nonimmunogenic stabilizers. Effective amounts of these additional components will be amounts which are sufficient to obtain pharmaceutically acceptable formulations in terms of solubility of components and biological activity, to name a few considerations.

By this invention, it has been found that administration of FEAU by either intravenous injection or orally at doses as low as 1 mg/kg/day prevents the development of rash and reduced viremia in monkeys infected with simian varicella virus. It has further been found that this effective dose can be further reduced to 0.2 mg/kg/day when administered in combination with a sub-effective dose of Hu rIFNβ. No adverse effects of the combination treatment were evident in daily clinical observations of the monkeys or in hematology and clinical chemistry tests performed during the entire course of this study. Similarly, neither FEAU or Hu IFNβ had any adverse effects when administered alone. Based upon this study with a monkey animal model, it is apparent that FEAU and Hu rIFNβ will exhibit similar synergy when used to treat viral infections in human patients. It is further apparent that other halogenated pyrimidines and Hu rIFNβ will exhibit similar synergy.

A suitable dosage range for human treatment with FEAU is less than 20.0 mg/kg/day, preferably about 0.2 to 2.0 mg/kg/day and with Hu IFNβ is about $1 \times 10^5$ to $90 \times 10^6$ IU/day. Suitable doses for the halogenated pyrimidines in general, are less than for FEAU because of their greater toxicity. Therefore, a suitable dose would be less than 0.2 mg/kg/day, with the range of Hu IFNβ being about $1 \times 10^5$ to $90 \times 10^6$ IU/day. The following examples best illustrate the embodiments of the invention.

Monkeys

African green monkeys (Cercopithecus aethiops) were selected as the animal model and were purchased as feral animals and stabilized during a 90 day quarantine period before use. It was determined that each of the monkeys was free of antibody to simian varicella virus by a serum neutralization assay performed prior to virus inoculation.

Simian Varicella Virus

The stock simian varicella virus was maintained in a pool of Vero cells infected by co-cultivation with lymphocytes from an infected monkey. The cultures were subsequently expanded by 5 passages as 1:3 splits of infected cells to fresh Vero cell cultures. The stock virus was prepared as a large pool of infected Vero cells sedimented by centrifugation and suspended in a solution of 0.2 M sucrose, 0.01 M $NaH_2PO_4$ and 1% bovine serum albumin and stored frozen at $-70°$ C. in 1 ml aliquots.

FEAU 1-(2'-Deoxy-2'-fluoro-1-β-D-arabinofuranosyl)-5-ethyl uracil (FEAU) was prepared at concentrations for appropriate doses by dissolution in distilled water and sterilized by filtration through a 0.22 μm filter for intravenous administration. FEAU for oral administration was not filtered. Solutions of FEAU were prepared daily for use.

Hu rIFNβ

Human recombinant interferon-beta (Hu rIFNβ) was provided by Triton Biosciences Inc. (Alameda, Calif.) in vials containing $54 \times 10^6$ IU per vial, and dissolved in sterile distilled water. Dilutions to the desired concentrations were prepared in phosphate buffered saline (PBS) pH 7.2, containing 0.5% human serum albumin. Hu rIFNβ was administered by bolus injection into the saphenous vein.

Simian Varicella Virus Infection

Monkeys were infected by inoculation of 1.5 ml of a dilution of stock virus by intratracheal catheter and by injection of 1.5 ml of this virus dilution subcutaneously. The intended dose was approximately $1 \times 10^5$ plaque forming units (PFU) of virus and the inoculum was titrated at the time of each experiment. Treatment with FEAU or Hu rIFNβ was begun 48 hours after virus inoculation and was administered in divided doses twice daily for 10 days.

Virus infection was monitered by observation of rash and by quantitation of viremia as described by Soike et al. in Antimicrob. Agents Chemother. 29: 20–25 (1986) and Soike et al. in J. Infect. Dis. 156: 607–614 (1987), incorporated herein by reference. Rash development was scored daily on a scale of +1 to +4 in relation to severity. Viremia was determined 3,5,7,9 and 11 days after virus inoculation by separating lymphocytes from a 3 ml heparinized blood specimen on a Lymphoprep ® gradient. The separated lymphocytes were washed twice in RPMI-1640 medium containing 15% fetal bovine serum and suspended in 10 ml of this medium. The 10 ml lymphocyte suspension was divided between two 25 $cm^2$ culture flasks containing Vero cells. Following 5 to 7 days incubation at 37° C. in a $CO_2$ incubator, the cell monolayers were washed with PBS, fixed in methanol, and stained with methylene blue-basic fuchsin. Developing plaques in each culture flask were counted and the mean number of plaques in the two flasks inoculated with each blood specimen was determined. Hematology and clinical chemistry tests were performed at 0,3,5,7,9 and 11 days after virus inoculation on all monkeys. Blood was drawn for determination of antibody titers to simian varicella virus at 14 and 21 days after virus inoculation. Monkeys dying during the course of the infection were given a complete necropsy and death as a consequence of simian varicella virus infection was confirmed by gross and histologic examination.

EXAMPLE I

An initial experiment to determine possible efficacy of FEAU comprised two groups of two monkeys each, which received either 10 or 3 mg/kg/day of FEAU by bolus intravenous injection. A control group of three monkeys received bolus intravenous injections of PBS. Treatment was administered in divided doses at 8 a.m. and 2 p.m., beginning 48 hours after virus inoculation and continuing for 10 days. Each of the three control monkeys developed severe infection with rash and high titered viremia resulting in death from systemic infection. FEAU at 10 or 3 mg/kg/day prevented the development of rash and effectively reduced viremia. Antibody to simian varicella virus was detected at moderate titers in the surviving monkeys. The data are presented in Table 1. Rash severity was noted on a scale of +1 to +4 at 6,7,8,9,10,11,12 and 14 days after virus inoculation, i.e., post-infection (P.I), and viremia was expressed as mean number of plaque forming units (PFU) developing in pairs of flasks of Vero cells inoculated with lymphocytes collected from 3 ml of heparinized blood at 3,5,7,9 and 11 days P.I.

TABLE 1

| FEAU mg/kg/day | NO. | Rash Severity on Days P.I. | | | | | | | |
|---|---|---|---|---|---|---|---|---|---|
| | | 6 | 7 | 8 | 9 | 10 | 11 | 12 | 14 |
| Control | G029 | 1+ | 1+ | 2+ | Dead | | | | |
| | G030 | — | 1+ | 3+ | 3+ | Dead | | | |
| | G031 | — | — | Dead | | | | | |
| 10 | G025 | — | — | — | — | — | — | — | — |
| | G026 | — | — | — | — | — | — | — | — |
| 3 | G027 | — | — | — | — | — | — | — | — |
| | G025 | — | — | — | — | — | — | — | — |

| | | Viremia, Mean PFU on days P.I. | | | | | Antibody Titer | |
|---|---|---|---|---|---|---|---|---|
| | | 3 | 5 | 7 | 9 | 11 | 14 days | 21 days |
| Control | G029 | 1 | 140 | >400 | Dead | | Dead | Dead |
| | G030 | 3 | 163 | >400 | >400 | Dead | Dead | Dead |
| | G031 | 1 | 99 | >400 | Dead | | Dead | Dead |
| 10 | G025 | 1 | 14 | 5 | 0 | 0 | 1:80 | 1:160 |
| | G026 | 0 | 1 | 1 | 0 | 0 | 1:10 | 1:160 |
| 3 | G027 | 1 | 8 | 0 | 0 | 0 | 1:40 | 1:160 |
| | G025 | 0 | 1 | 1 | 0 | 0 | 1:20 | 1:160 |

EXAMPLE II

Groups of three monkeys received FEAU at 1.0, 0.2 or 0.04 mg/kg/day by bolus intravenous injection as divided doses as in Example I. Three control monkeys were treated as in Example I. The three control monkeys developed moderate to moderately severe rash and moderate or severe viremia. One of the control monkeys died with disseminated varicella. The two surviving monkeys showed good antibody titers. FEAU at 1.0 mg/kg/day prevented the development of rash but was only minimally effective in inhibiting viremia with two of the three monkeys shown to have moderate titers of virus in the blood. Antibody titers to simian varicella virus were depressed in two of the monkeys. The lower doses of FEAU, 0.2 and 0.04 mg/kg/day, were ineffective and did not reduce either rash or viremia. One monkey at the lowest dose died of simian varicella virus infection. Appreciable antibody titers were observed in each of the surviving monkeys. The data are presented in Table 2 and were collected as in Example I.

TABLE 2

| FEAU mg/kg/day | NO. | Rash Severity on Days P.I. | | | | | | | |
|---|---|---|---|---|---|---|---|---|---|
| | | 6 | 7 | 8 | 9 | 10 | 11 | 12 | 14 |
| Control | G250 | — | 1+ | 2+ | 3+ | 3+ | 2+ | 1+ | ± |
| | G252 | — | — | — | ± | 2+ | 2+ | Dead | |
| | G253 | — | — | 1+ | 2+ | 3+ | 2+ | 1+ | — |
| 1.0 | G254 | — | — | — | — | — | — | — | — |
| | G255 | — | — | — | — | — | — | — | — |
| | G256 | — | — | — | — | — | — | — | — |
| 0.2 | G258 | — | 1+ | 2+ | 2+ | 3+ | 1+ | 1+ | ± |
| | G259 | — | ± | ± | ± | 2+ | 2+ | 1+ | — |
| | G260 | 1+ | 2+ | 3+ | 3+ | 4+ | 4+ | 4+ | 2+ |
| 0.04 | G261 | 2+ | 4+ | 4+ | 4+ | 4+ | Dead | | |
| | G262 | — | 1+ | 1+ | 2+ | 2+ | ± | — | — |
| | G263 | — | ± | 1+ | 2+ | 2+ | 3+ | 3+ | 3+ |

| | | Viremia, Mean PFU on days P.I. | | | | | Antibody Titer | |
|---|---|---|---|---|---|---|---|---|
| | | 3 | 5 | 7 | 9 | 11 | 14 days | 21 days |
| Control | G250 | 0 | 34 | 68 | 29 | 0 | 1:160 | 1:160 |
| | G252 | 2 | 25 | >400 | >400 | >400 | Dead | Dead |
| | G253 | 1 | 11 | 107 | 36 | 1 | 1:320 | 1:640 |
| 1.0 | G254 | 1 | 2 | 134 | 20 | 1 | 1:320 | 1:320 |
| | G255 | 3 | 8 | 109 | 14 | 2 | 1:10 | 1:40 |
| | G256 | 1 | 3 | 7 | 6 | 6 | 1:40 | 1:80 |
| 0.2 | G258 | 2 | 8 | 16 | 36 | 1 | 1:160 | 1:320 |
| | G259 | 1 | 6 | 365 | 68 | 0 | ≧1:320 | 1:640 |
| | G260 | 2 | 2 | >400 | 159 | 2 | 1:160 | 1:640 |
| 0.04 | G261 | 3 | 3 | >400 | >400 | Dead | Dead | Dead |
| | G262 | 4 | 53 | 92 | 46 | 2 | 1:320 | ≧1:640 |
| | G263 | 12 | 44 | >400 | >400 | 2 | 1:160 | ≧1:640 |

EXAMPLE III

Oral administration of FEAU was studied and found to be highly effective in protecting the monkeys from simian varicella virus infection. Groups of three monkeys were treated with 10, 3 or 1 mg/kg/day of FEAU with treatment beginning 48 hours after virus inoculation. Treatment was administered orally as divided doses twice daily and continuing for 10 days. The control group comprised three monkeys who did not receive FEAU. Two of the control monkeys developed severe rash and the third had a moderate rash. Viremia was severe in one control monkey that died as a result of infection. The two remaining control monkeys has a mild viremia. FEAU at each of the three doses completely prevented the appearance of rash. Viremia was also inhibited by FEAU at each of the three dose levels. Only one monkey at the lowest dose (1 mg/kg/day) showed a mild viremia. The data are presented in Table 3 and were collected as in Example I.

TABLE 3

| FEAU mg/kg/day | NO. | Rash Severity on Days P.1. | | | | | | | |
|---|---|---|---|---|---|---|---|---|---|
| | | 6 | 7 | 8 | 9 | 10 | 11 | 12 | 14 |
| Control | F644 | ± | 3+ | 4+ | 4+ | Dead | | | |
| | G668 | — | — | ± | 2+ | 1+ | ± | ± | — |
| | G604 | — | ± | 3+ | 4+ | 4+ | 2+ | 1+ | 1+ |
| 10 | G249 | — | — | — | — | — | — | — | — |
| | G267 | — | — | — | — | — | — | — | — |
| | G264 | — | — | — | — | — | — | — | — |
| 3 | G265 | — | — | — | — | — | — | — | — |
| | G257 | — | — | — | — | — | — | — | — |
| | G268 | — | — | — | — | — | — | — | — |
| 1 | G269 | — | — | — | — | — | — | — | — |
| | G270 | — | — | — | — | — | — | — | — |
| | G274 | — | — | — | — | — | — | — | — |

| | | Viremia, Mean PFU on days P.I. | | | | Antibody Titer | |
|---|---|---|---|---|---|---|---|
| | | 3 | 7 | 9 | 11 | 14 days | 21 days |
| Control | F644 | 38 | >400 | >400 | Dead | Dead | Dead |
| | G668 | 8 | 32 | 29 | 25 | 1:320 | 1:640 |
| | G604 | 24 | 16 | 39 | 34 | ≧1:320 | ≧1:640 |

TABLE 3-continued

| | | | | | | | |
|---|---|---|---|---|---|---|---|
| 10 | G249 | 2 | 0 | 0 | 0 | <1:10 | 1:20 |
| | G267 | 5 | 1 | 1 | 0 | 1:80 | 1:160 |
| | G264 | 15 | 1 | 3 | 5 | 1:40 | 1:80 |
| 3 | G265 | 7 | 13 | 9 | 10 | 1:160 | 1:320 |
| | G257 | 3 | 5 | 1 | 4 | 1:80 | 1:160 |
| | G268 | 5 | 1 | 0 | 1 | 1:80 | 1:160 |
| 1 | G269 | 0 | 0 | 2 | 0 | 1:80 | 1:80 |
| | G270 | 0 | 2 | 2 | 3 | 1:160 | 1:320 |
| | G274 | 7 | 47 | 7 | 7 | 1:160 | 1:320 |

EXAMPLE IV

Experiments to determine the effects of the combination of FEAU with Hu rIFN$\beta$ were performed as a series of six experiments and the data pooled for analysis. Each treatment group receiving FEAU or Hu rIFN$\beta$ alone or the various combinations of FEAU and Hu rIFN$\beta$ contained four or five monkeys. The mean viremia for each of these groups are presented in Table 4. FEAU was administered orally by stomach tube beginning 48 hours after virus inoculation and continuing as divided daily doses for 10 days. Hu rIFN$\beta$ was given by intravenous bolus injection as divided doses beginning 48 hours after virus inoculation. FEAU administered alone at each of the three doses resulted in appreciable viremia on post-infection days 7 and 9. Similarly, Hu rIFN$\beta$ given alone permitted substantial viremia on days 7 and 9. The combination of FEAU and Hu rIFN$\beta$ employing the lowest doses resulted in high titered viremia on days 5 and 7. The combinations at the higher doses were highly effective in reducing viremia on each of the days of assay.

TABLE 4

| Combined Treatment | | Viremia Assay | | | |
|---|---|---|---|---|---|
| FEAU | Hu rIFN$\beta$ | Mean PFU on Days Post-Infection | | | |
| mg/kg/day | IU/kg/day | Day 3 | Day 5 | Day 7 | Day 9 |
| 0 | 0 | 10.4 | 111.4 | 710.0 | 589.1 |
| 0.05 | 0 | 2.7 | 23.3 | 383 | 261 |
| 0.2 | 0 | 11.2 | 95.8 | 295 | 197 |
| 1.0 | 0 | 55.3 | 40.8 | 256 | 251 |
| 0 | 2.5 × 10³ | 34.3 | 199 | 370 | 561 |
| 0 | 1.0 × 10⁴ | 10.8 | 136 | 169 | 200 |
| 0 | 5.0 × 10⁴ | 6.6 | 28 | 611 | 41 |
| 0.05 | 2.5 × 10³ | 20.3 | 131 | 394 | 25.3 |
| 0.2 | 1.0 × 10⁴ | 3.6 | 36.6 | 32.3 | 3.2 |
| 1.0 | 5.0 × 10⁴ | 2.13 | 4.3 | 0.5 | 0.5 |

EXAMPLE V

A computer program was used for analysis of the combined effects of FEAU and Hu rIFN$\beta$ using the median effect equation and determination of the combination index (CI) as established by Chou et al. in Advances in Enzyme Regulation 22: 27–55 (1984) and Chou et al. in "Dose-Effect Analysis with Microcomputers: Quantitation of ED$_{50}$, LD$_{50}$, Synergism, Antagonism, Low-dose Risk, Receptor Ligand Binding and Enzyme Kinetics", IBM-PC Series (Elsevier Science Publishers, Cambridge, U.K., 1986), incorporated herein by reference. The analysis employed constant ratios of FEAU to Hu rIFN$\beta$ and used data from the viremia values for days 5,7 and 9. The analysis is based on the median effect equation $f_a/f_u = (C/C_m)^m$ where $f_a$ and $f_u$ are the fractions of the system which are affected and unaffected, C is the concentration, $C_m$ is the concentration which produces the median effect and m is the slope of the dose-effect plots. The combination index (CI) is calculated based upon the compounds being mutually exclusive or mutually nonexclusive. The CI values determined from the median-effect plot of <1, =1 or >1 indicate synergism, additivism or antagonism, respectively, and are based on the classical isobologram equation.

Results of analysis of the data for synergy with determination of the combination index are reported in Table 5. Values given are based on the classical isobologram equation and the values in parentheses are based on the conservative isobologram equation. FEAU was administered orally and Hu rIFN$\beta$ was administered by intravenous injection. The lowest doses of FEAU and Hu rIFN$\beta$ administered in combination did not result in synergy. Data obtained from analysis of the low dose monkeys on days 5 and 9 essentially showed an additive effect with a CI of about 1, while data from day 7 showed antagonism with a CI of 4.72. Analysis of viremia data from the mid- and high-dose combinations showed strong synergism (CI less than 1) particularly on days 7 and 9. Results on day 5 indicated synergism which was less dramatic.

TABLE 5

| Combination Treatment | | Viremia Assay | | | | | |
|---|---|---|---|---|---|---|---|
| FEAU mg/kg/day | Hu rIFN$\beta$ IU/kg/day | Day 5 | | Day 7 | | Day 9 | |
| | | $f_a$ | CI | $f_a$ | CI | $f_a$ | CI |
| 0.05 | 2.5 × 10³ | <0.02 | 1.28 (1.53) | 0.445 | 4.72 (4.72) | 0.571 | 1.12 (1.34) |
| 0.2 | 1.0 × 10⁴ | 0.672 | 0.404 (0.445) | 0.955 | 0.125 (0.125) | 0.995 | 0.035 (0.035) |
| 1.0 | 5.0 × 10⁴ | 0.962 | 0.664 (0.745) | 0.999 | 0.006 (0.006) | 0.999 | 0.049 (0.049) |

I claim:

1. A composition having a synergistic antiviral effect on viral infections comprising synergistically antiviral effective amounts of human recombinant interferon-beta and a fluorinated pyrimidine selected from the group consisting of FEAU, FMAU, FIAU, and FIAC.

2. The composition of claim 1 wherein said human recombinant interferon-beta is produced from E. coli or Chinese hamster ovary cells.

3. The composition of claim 1 wherein said human recombinant interferon-beta is a mutein of interferon-beta having the cysteine residue at position 17 of interferon-beta replaced by a serine residue.

4. The composition of claim 1 wherein said viral infection is a herpes virus.

5. A method of treating human viral infections by combination therapy of synergistically antiviral effective amounts of interferon-beta and a fluorinated pyrimidine selected from the group consisting of FEAU, FMAU, FIAU, FIAC.

6. The method of claim 5 wherein said human recombinant interferon-beta is produced from E. coli or Chinese hamster ovary cells.

7. The method of claim 5 wherein said human recombinant interferon-beta is a mutein of interferon-beta having the cysteine residue at position 17 of interferon-beta replaced by a serine residue.

8. The method of claim 5 wherein said fluorinated pyrimidine and said human recombinant inteferon-beta are administered simultaneously.

9. The method of claim 8 wherein said composition further comprises a pharmaceutically acceptable diluent or carrier.

10. The method of claim 5 wherein said fluorinated pyrimidine and said human recombinant interferon-beta are administered separately.

11. The method of claim 10 wherein said fluorinated pyrimidine and said human recombinant interferon-beta are contained in separate compositions of matter, each comprising a pharmaceutically acceptable diluent or carrier.

12. The method of claim 5 wherein said viral infection is a herpes virus.

13. A pharmaceutical composition having a synergistic antiviral effect on viral infections comprising synergistically antiviral effective amounts of p1 (a) human recombinant interferon-beta,
  (b) a fluorinated pyrimidine selected from the group consisting of FEAU, FMAU, FIAU, and FIAC, and
  (c) a pharmaceutically acceptable diluent or carrier.

14. The composition of claim 13 wherein said human recombinant interferon-beta is produced from *E. coli* or Chinese hamster ovary cells.

15. The composition of claim 13 wherein said human recombinant interferon-beta is a mutein of interferon-beta having the cysteine residue at position 17 of interferon-beta replaced by a serine residue.

16. The composition of claim 13 wherein said viral infection is a herpes virus.

17. A method of treating viral infections by parenterally administering a synergistically antiviral effective amount of interferon-beta and orally administering a synergistically antiviral effective amount of a fluorinated pyrimidine selected from the group consisting of FEAU, FMAU, FIAU, FIAC.

18. The method of claim 17 wherein said human recombinant interferon-beta is produced from *E. coli* or Chinese hamster ovary cells.

19. The method of claim 17 wherein said human recombinant interferon-beta is a mutein of interferon-beta having a cysteine residue at position 17 of interferon-beta replaced by a serine residue.

20. The method of claim 17 wherein said parenteral administration is intravenous.

21. The method of claim 17 wherein said parenteral administration is subcutaneous.

22. The method of claim 17 wherein said parenteral administration is intramuscular.

23. The method of claim 17 wherein said viral infection is a herpes virus.

24. A composition having a synergistic antiviral effect on viral infections comprising synergistically antiviral effective amounts of FEAU and human recombinant interferon-beta.

25. A method of treating human viral infections by a combination therapy of synergistically antiviral effective amounts of FEAU and human recombinant interferon-beta.

26. A pharmaceutical composition having a synergistic antiviral effect on viral infections comprising synergistically antiviral effective amounts of FEAU and human recombinant interferon-beta together with a pharmaceutically acceptable diluent or carrier.

27. A method of treating viral infections by orally administering a synergistically antiviral effective amount of FEAU and parenterally administering a synergistically antiviral effective amount of human recombinant interferon-beta.

28. The composition of claim 26, wherein the FEAU and human recombinant interferon-beta are in a ratio in the range of about 0.2 to 2.0 mg FEAU per kg of subject to about $1 \times 10^5$ to $90 \times 10^6$ IU of interferon-beta.

29. The composition of claim 28, wherein said composition is in a daily unit dose providing between about $1 \times 10^5$ to $90 \times 10^6$ IU of interferon-beta.

30. The method of claim 25, wherein the FEAU and human recombinant interferon-beta are in a ratio in the range of about 0.2 to 2.0 mg FEAU per kg of subject to about $1 \times 10^5$ to $90 \times 10^6$ IU of interferon-beta.

31. The method of claim 30, wherein said FEAU and human interferon-beta are together in a daily unit dose providing between about $1 \times 10^5$ to $90 \times 10^6$ IU of interferon-beta.

* * * * *